United States Patent [19]  [11] 4,431,803
Kukolja et al.  [45] Feb. 14, 1984

[54] 7-EPI 3-EXOMETHYLENECEPHAMS

[75] Inventors: Stjepan Kukolja, Carmel; Janice L. Pfeil, Indianapolis, both of Ind.

[73] Assignee: Eli Lilly and Company, Indianapolis, Ind.

[21] Appl. No.: 333,156

[22] Filed: Dec. 21, 1981

[51] Int. Cl.³ ............... C07D 501/22; A61K 31/545
[52] U.S. Cl. ...................................... 544/16; 544/22; 424/246
[58] Field of Search ............................ 544/16, 21, 22; 424/246

[56] References Cited

U.S. PATENT DOCUMENTS 3,792,995  2/1974  Ochiai et al. .......... 204/72
4,031,084  6/1977  Kukolja et al. ........ 544/16
4,042,472  8/1977  Hall .................... 204/73
4,060,688 11/1977  Chauvette ............. 544/16

OTHER PUBLICATIONS

Chauvette and Pennington, J. Org. Chem. 38, 2994–2999, (1973).

Primary Examiner—Nicholas S. Rizzo
Attorney, Agent, or Firm—Joseph A. Jones; Arthur R. Whale

[57] ABSTRACT

7-Epi-3-exomethylenecephams are useful intermediates for synthesis of antibiotics.

14 Claims, No Drawings

7-EPI 3-EXOMETHYLENECEPHAMS

BACKGROUND OF THE INVENTION

1. Field of the Invention

This invention belongs to the field of pharmaceutical chemistry, and provides a series of new intermediates for the synthesis of antibiotically active cephalosporin compounds and other substances. The new compounds are exomethylenecephams, wherein the side chain at the 7-position of the cephalosporin nucleus is in the α configuration, rather than the β configuration of natural cephalosporins.

2. State of the Art

Exomethylenecephams have long been known in pharmaceutical chemistry, and have long been used as convenient intermediates. See, for example, the article by Chauvette and Pennington, *J. Org. Chem* 38, 2994 (1973), where the synthesis of such compounds was discussed.

Exomethylenecephams wherein the side chain at the 7-position is in the α configuration have not heretofore been available, because the accepted procedures for epimerizing the compounds changed the exomethylenecepham to a 3-methylcephem. The known epimerizations of the cephalosporin and penicillin side chain take place in the presence of strong bases; see, for example, Flynn, Cephalosporins and Penicillins, Academic Press, New York, 1972, pages 105-19. For example, see page 2996 of the Chauvette and Pennington article, where treatment with a strong base is shown to convert an exomethylenecepham to the 3-methylcephem.

SUMMARY OF THE INVENTION

This invention provides novel 7-epi-exomethylenecephams of the formula

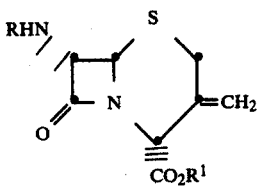

wherein R is hydrogen or an acyl group derived from a carboxylic acid, and $R^1$ is hydrogen, a carboxy-protecting group, or a salt-forming cation.

DESCRIPTION OF THE PREFERRED EMBODIMENTS

In this document, all temperatures are stated in degrees Celsius. All percentages, ratios, concentrations and the like are stated in weight units unless otherwise described.

In the formula above, the group $R^1$ completes an acid or a salt, or is a carboxy-protecting group forming an ester. Such forms of cephalosporin compounds are conventional; in the context of this invention, which provides exomethylenecephams useful as intermediates for further processing, the compounds wherein $R^1$ is a carboxy-protecting group are preferred, because of their value as intermediates.

The compounds where $R^1$ is a salt-forming cation, however, and the acids wherein $R^1$ is hydrogen, are also valuable. Particularly useful cations include such commonly used salt-forming moieties as sodium, potassium, lithium, ammonium and the like.

In the antibiotic art, the term "carboxy-protecting group" refers to any suitable group used to block or protect the cephalosporin carboxylic acid functionality while reactions involving other functional sites are carried out. Such carboxylic acid-protecting groups are noted for their ease of cleavage, as for example by hydrolytic or hydrogenolytic methods to the corresponding carboxylic acid. Examples of suitable carboxylic acid-protecting groups are tert-butyl, 1-methylcyclohexyl, benzyl, 4-methoxybenzyl, 4-nitrobenzyl, acetoxymethyl, 1-acetoxyethyl, pivaloyloxymethyl, 1-pivaloyloxyethyl, carboethoxyoxymethyl, 1-carboethoxyoxyethyl, phthalidyl, 2-iodoethyl, 2-bromoethyl, benzhydryl, phenacyl, 4-halophenacyl, dimethylallyl, 2,2,2-trichloroethyl, methoxymethyl, tri($C_1$–$C_3$ alkyl)silyl and succinimidomethyl. Other known carboxylic acid-protecting groups are described by E. Haslam in "Protective Groups in Organic Chemistry," J. F. W. McOmie, Ed., Plenum Press, New York, 1973, Chapter 5. The nature of such groups is not critical; however, because of availability, ease of handling and other desirable properties, certain carboxylic acid-protecting groups are preferred. A preferred selection of carboxylic acid-protecting groups includes acetoxymethyl, 1-acetoxyethyl, pivaloyloxymethyl, 1-pivaloyloxyethyl, carboethoxyoxymethyl, 1-carboxyethoxyoxyethyl, phthalidyl, diphenylmethyl, nitrobenzyl, tert-butyl, methoxybenzyl, trichloroethyl, and methyl.

The group R in the above general formula is hydrogen or an acyl group derived from a carboxylic acid, and, more particularly, is a group conventionally used in the cephalosporin art. This invention provides no new R groups, but makes use of those conventionally used by cephalosporin chemists in making antibiotically active compounds and intermediates for their synthesis. Preferred R groups, however, include those of the formula $R^2OC$, wherein $R^2$ is hydrogen, $C_1$–$C_3$ alkyl, cyanomethyl, benzyloxy, 4-nitrobenzyloxy, t-butoxy, 2,2,2-trichloroethoxy, 4-methoxybenzyloxy, or the group $R^3$, in which $R^3$ is phenyl or phenyl substituted by 1 or 2 halogen, protected hydroxy, nitro, cyano, trifluoromethyl, $C_1$–$C_4$ alkyl or $C_1$–$C_4$ alkoxy groups; or $R^2$ is a group of the formula $R^4$—(O)$_n$—$CH_2$—, in which $R^4$ has the same meanings as $R^3$ above, or is 1,4-cyclohexadienyl, 2-thienyl or 3-thienyl; n is 0 or 1; provided that when n is 1, $R^4$ has the same meanings as $R^3$; or $R^2$ is a group of the formula $R^4$—CH(W)—, wherein $R^4$ has the same meanings as defined above, and W is protected hydroxy or protected amino.

A more preferred class of $R^2$ groups includes $C_1$–$C_3$ alkyl, phenyl, phenoxymethyl, benzyl, and phenyl substituted with $C_1$–$C_4$ alkyl, especially with methyl.

In the above definitions, the terms $C_1$–$C_3$ alkyl, $C_1$–$C_4$ alkoxy and $C_1$–$C_4$ alkyl have their usual meanings in the organic chemical literature, and include groups such as methyl, methoxy, ethyl, ethoxy, propyl, isopropoxy, isobutyl, s-butoxy and the like.

The term protected amino refers to an amino group substituted with one of the commonly employed amino-protecting groups such as t-butoxycarbonyl, benzyloxycarbonyl, 4-methoxybenzyloxycarbonyl, 4-nitrobenzyloxycarbonyl, 2,2,2-trichloroethoxycarbonyl and 1-carbomethoxy-2-propenyl. Other accepted amino-protecting groups such as are described by J. W. Barton in *Protective Groups in Organic Chemistry*, Chapter 2 will be recognized by organic chemists as suitable for the purpose.

Similarly, the term protected hydroxy refers to groups formed with a hydroxy group such as formyloxy, 2-chloroacetoxy, benzyloxy, diphenylmethoxy, triphenylmethoxy, 4-nitrobenzyloxy, trimethylsilyloxy, phenoxycarbonyloxy, t-butoxy, methoxymethoxy and tetrahydropyranyloxy. Other accepted hydroxy-protecting groups, such as those described by C. B. Reese in Chapter 3 of *Protective Groups in Organic Chemistry* will be understood to be included in the term protected hydroxy.

It is believed that the 7-epi-exomethylenecephams of this invention are clearly and fully described by the above discussion. However, a few typical compounds provided by the invention will be named, to assure that the reader fully understands the invention.

t-butyl 7-α-acetamido-3-exomethylenecepham-4-carboxylate benzyl 7-α-butyramido-3-exomethylenecepham-4-carboxylate 4-methoxybenzyl 7-α-(2-methylpropionamido)-3-exomethylenecepham-4-carboxylate 1-methylcyclohexyl 7-α-cyanoacetamido-3-exomethylenecepham-4-carboxylate 4-nitrobenzyl 7-α-benzyloxyformamido-3-exomethylenecepham-4-carboxylate acetoxymethyl 7-α-(4-nitrobenzyloxyformamido)-3-exomethylenecepham-4-carboxylate 1-acetoxyethyl 7-α-t-butoxyformamido-3-exomethylenecepham-4-carboxylate t-butoxymethyl 7-α-(2,2,2-trichloroethoxyformamido)-3-exomethylenecepham-4-carboxylate 4-chlorobenzoylmethyl 7-α-amino-3-exomethylenecepham-4-carboxylate 2-iodoethyl 7-α-(4-methoxybenzyloxyformamido)-3-exomethylenecepham-4-carboxylate 2-bromoethyl 7-α-phenylformamido-3-exomethylenecepham-4-carboxylate diphenylmethyl 7-α-(3-chlorophenylformamido)-3-exomethylenecepham-4-carboxylate ethoxycarbonyloxymethyl 7-α-(4-formyloxyphenylformamido)-3-exomethylenecepham-4-carboxylate methoxymethyl 7-α-(2-nitrophenylformamido)-3-exomethylenecepham-4-carboxylate trimethylsilyl 7-α-(3-cyanophenylformamido)-3-exomethylenecepham-4-carboxylate 2,2,2-trichloroethyl 7-α-(4-trifluoromethylphenylformamido)-3-exomethylenecepham-4-carboxylate phthalimidomethyl 7-α-(3-methylphenylformamido)-3-exomethylenecepham-4-carboxylate succinimidomethyl 7-α-(4-propylphenylformamido)-3-exomethylenecepham-4-carboxylate 2-pivaloyloxyethyl 7-α-(3-isobutylphenylformamido)-3-exomethylenecepham-4-carboxylate 2,2,2-tribromoethyl 7-α-(4-methoxyphenylformamido)-3-exomethylenecepham-4-carboxylate 1-acetoxypropyl 7-α-(2-ethoxyphenylformamido)-3-exomethylenecepham-4-carboxylate 7-α-(3-t-butoxyphenylformamido)-3-exomethylenecepham-4-carboxylic acid sodium 7-α-(3-chloro-4-fluorophenylformamido)-3-exomethylenecepham-4-carboxylate potassium 7-α-(2-bromo-5-chloroacetoxyphenylformamido)-3-exomethylenecepham-4-carboxylate lithium 7-α-[3,5-bis(t-butoxy)phenyl]formamido-3-exomethylenecepham-4-carboxylate ammonium 7-α-(tetrazol-1-yl)formamido-3-exomethylenecepham-4-carboxylate 7-α-(4-iodo-3-nitrophenylformamido)-3-exomethylenecepham-4-carboxylic acid ammonium 7-α-(4-phenoxycarbonyloxy-2-cyanophenylformamido)-3-exomethylenecepham-4-carboxylate 7-α-(3-nitro-5-cyanophenylformamido)-3-exomethylenecepham-4-carboxylic acid 2,2,2-trichloroethyl 7-α-(3,5-dinitrophenylformamido)-3-exomethylenecepham-4-carboxylate 2-bromoethyl 7-α-(3-nitro-4-trifluoromethylphenylformamido)-3-exomethylenecepham-4-carboxylate sodium 7-α-(2-methyl-4-trifluoromethylphenylformamido)-3-exomethylenecepham-4-carboxylate diphenylmethyl 7-α-(3,4-diethylphenylformamido)-3-exomethylenecepham-4-carboxylate 4-nitrobenzyl 7-α-amino-3-exomethylenecepham-4-carboxylate 7-α-([3,5-bis(isopropoxy)phenylformamido]-3-exomethylenecepham-4-carboxylic acid trimethylsilyl 7-α-(2-bromo-5-s-butylphenylformamido)-3-exomethylenecepham-4-carboxylate 4-methoxybenzyl 7-α-(1,4-cyclohexadienylacetamido)-3-exomethylenecepham-4-carboxylic acid phthalimidomethyl 7-α-(thien-2-ylacetamido)-3-exomethylenecepham-4-carboxylate t-butyl 7-α-phenylacetamido-3-exomethylenecepham-4-carboxylic acid 7-α-phenoxyacetamido-3-exomethylenecepham-4-carboxylic acid potassium 7-α-(4-chlorophenoxyacetamido)-3-exomethylenecepham-4-carboxylate 7-α-(2,4-diiodophenylacetamido)-3-exomethylenecepham-4-carboxylic acid diphenylmethyl 7-α-(4-bromo-3-t-butoxyphenoxyacetamido)-3-exomethylenecepham-4-carboxylate 7-α-(3-chloro-2-nitrophenylacetamido)-3-exomethylenecepham-4-carboxylic acid benzyl 7-α-(3-cyano-5-trifluoromethylphenoxyacetamido)-3-exomethylenecepham-4-carboxylic acid acetoxymethyl 7-α-(2-cyano-4-iodophenylacetamido)-3-exomethylenecepham-4-carboxylate ethoxycarbonyloxymethyl 7-α-(4-benzyloxy-3-ethylphenoxyacetamido)-3-exomethylenecepham-4-carboxylate potassium 7-α-(3,4-dinitrophenylacetamido)-3-exomethylenecepham-4-carboxylate 4-methoxybenzyl 7-α-(3,4-dicyanophenoxyacetamido)-3-exomethylenecepham-4-carboxylate 7-α-(3-iodo-4-propoxyphenylacetamido)-3-exomethylenecepham-4-carboxylic acid 7-α-(2,4-dimethoxyphenoxyacetamido)-3-exomethylenecepham-4-carboxylic acid 2,2,2-trichloroethyl 7-α-(2-isopropyl-4-methylphenoxyacetamido)-3-exomethylenecepham-4-carboxylate 7-α-[2,4-bis(trimethylsilyl)phenoxyacetamido]-3-exomethylenecepham-4-carboxylic acid 4-nitrobenzyl 7-α-(4-formyloxyphenoxyacetamido)-3-exomethylenecepham-4-carboxylic acid trimethylsilyl 7-α-(3-nitrophenoxyacetamido)-3-exomethylenecepham-4-carboxylate potassium 7-α-(4-cyanophenylacetamido)-3-exomethylenecepham-4-carboxylate lithium 7-α-(2-trifluoromethylphenoxyacetamido)-3-exomethylenecepham-4-carboxylate 7-α-(4-ethylphenylacetamido)-3-exomethylenecepham-4-carboxylic acid 7-α-(3-propoxyphenoxyacetamido)-3-exomethylenecepham-4-carboxylic acid 4-methoxybenzyl 7-α-[chloroacetoxy(1,4-cyclohexadienyl)acetamido]-3-exomethylenecepham-4-carboxylate 1-methylcyclohexyl 7-α-[t-butoxyformamido(1,4-cyclohexadienyl)acetamido]-3-exomethylenecepham-4-carboxylate trimethylsilyl 7-α-[(thien-2-yl)(4-methoxybenzyloxyformamido)acetamido]-3-exomethylenecepham-4-carboxylate 7-α-[(thien-2-yl)trimethylsilyloxyacetamido]-3-exomethylenecepham-4-carboxylic acid acetoxymethyl 7-α-[phenyl(4-nitrobenzyloxyformamido)acetamido]-3-exomethylenecepham-4-carboxylate 7-α-[phenyl(benzyloxy)acetamido]-3-exomethylenecepham-4-carboxylic acid 7-α-[benzyloxyformamido(4-bromophenyl)acetamido]-3-exomethylenecepham-4-carboxylic acid 7-α-[trimethylsilyloxy(4-trimethylsilyloxyphenyl)acetamido]-3-exomethylenecepham-4-carboxylic acid 4-methoxybenzyl 7-α-[t-butoxy(3-nitrophenyl)acetamido]-3-exomethylenecepham-4-carboxylate acetoxymethyl 7-α-[(4-cyanophenyl)(2,2,2-trichloroethoxyformamido)acetamido]-3-exomethylenecepham-4-carboxylate 7-α-[benzyloxyformamido(2-nitrophenyl)acetamido]-3-exomethylenecepham-4-carboxylic acid 7-α-[(4-trifluoromethylphenyl)(4-nitrobenzyloxyformamido)acetamido]-3-exomethylenecepham-4-carboxylic acid 7-α-[diphenylmethoxy(4-methylphenyl)acetamido]-3-exomethylenecepham-4-carboxylic acid trimethylsilyl 7-α-[triphenylmethoxy(4-t-butylphenyl)acetamido]-3-exomethylenecepham-4-carboxylate 4-chlorobenzoylmethyl 7-α-[phenoxycarbonyloxy(3-ethoxyphenyl)acetamido]-3-exomethylenecepham-4-carboxylate 7-α-[methoxymethoxy(4-s-butoxyphenyl)acetamido]-3-exomethylenecepham-4-carboxylic acid 7-α-[t-butoxyformamido(2,4-difluorophenyl)acetamido]-3-exomethylenecepham-4-carboxylic acid 7-α-[benzyloxyformamido[3,5-bis(trifluoromethyl)phenyl]acetamido]-3-exomethylenecepham-4-carboxylic acid 4-nitrobenzyl 7-α-[trimethylsilyloxy(2,5-diethylphenyl)acetamido]-3-exomethylenecepham-4-carboxylate 4-methoxybenzyl 7-α-[diphenylmethoxy(2-chloro-3cyanophenyl)acetamido]-3-exomethylenecepham-4-carboxylate 4-methoxybenzyl 7-α-[formyloxy(3-formyloxy-4-nitrophenyl)acetamido]-3-exomethylenecepham-4-carboxylate diphenylmethyl 7-α-[t-butoxyformamido(2-methoxy-4-trifluoromethylphenyl)acetamido]-3-exomethylenecepham-4-carboxylate The most preferred group of compounds of this invention are those wherein R represents one of the following:
(a) hydrogen,
(b) phenoxyacetyl,
(c) phenylacetyl, or
(d) 4-methylphenylformyl;

and $R^1$ represents one of the following:
(a) hydrogen,
(b) 4-nitrobenzyl,
(c) 4-methoxybenzyl,
(d) diphenylmethyl, or
(e) 2,2,2-trichloromethyl.

The compounds of the present invention are made by various processes. The preferred process is the electrolytic reduction of the corresponding 3-acetoxymethyl epi configuration cephem, or its sulfoxide. Examples 5 and 6 below illustrate the process. The electrolytic transformation of 3-acetoxymethyl cephalosporins to 3-exomethylene compounds finds precedent in the art, as shown by U.S. Pat. Nos. 3,792,995, of Ochiai et al., and 4,042,472, of Hall.

It should be noted that, if the electrolytic process is used on a starting compound having a nitrobenzyl protecting group, that protecting group will be cleaved, at least to some extent. The cleavage of the protecting group may be an advantage, in some circumstances; if not, it can readily be avoided by merely using a different protecting group.

When the starting compound for the electrolytic reduction is a sulfoxide, the electrolysis reduces the 1-oxide to the desired sulfide form, as in Ex. 6 below.

The electrolytic cells used are the conventional types now known in the electrochemical art. Some discussion of electrolytic cells will be given, however.

An electrolytic cell of the type used for electrolytic reductions has a working electrode, sometimes called the cathode, at which the reduction takes place. The working electrode is maintained at a potential which is negative with respect to the auxiliary electrode, or anode, at which only electrolyte reactions should take place. A reference electrode is usually used, also. The reference electrode, at which no reactions should take place, supplies a reference point from which the potential of the working electrode is measured. A typical and frequently-used reference electrode is the saturated calomel electrode; others are the mercury/mercuric oxide electrode and the silver/silver chloride electrode. The reference electrode is electrically connected to the working fluid through a conductive bridge or a porous junction.

Cells are very often divided into compartments, so that each of the electrodes is immersed in fluid which is physically separated from the fluids of the other compartments, but is electrically connected to them. Such division of the cell is optional in the context of the present invention, unless the compound to be reduced bears a group which can be electrically oxidized. The oxidizability of the starting compound may be readily determined by running a voltammogram on the auxiliary electrode in a positive direction with respect to the reference electrode. The presence of inflection points indicates that one or more oxidizable groups are present and that a divided cell is necessary, so that the auxiliary electrode is physically separated from the working fluid which contains the compound.

The arrangement of electrolytic cells, the construction of electrodes, and the materials which may be effectively used as dividers are all part of the common knowledge of the electrochemical art, and may easily be learned by reference to text books and journal articles. Particularly useful text books which may be mentioned include Organic Electrochemistry, M. M. Baizer, Editor, Marcel Dekker, Inc., New York (1973), and Technique of Electroorganic Synthesis, N. L. Weinberg, Editor, John Wiley and Sons, New York (1974).

Working electrodes for use in the process of this invention are made of carbon, mercury, tin, aluminum, copper, lead, chromium, zinc, nickel or cadmium. The preferred working electrodes are mercury, silver and lead. The electrodes should be rather highly purified, as is normally the case in electrochemistry. The form of the electrode is not important; it may be solid sheet, gauze or cloth, a basket of shot, or a fluidized bed of particles, with equally good results. The electrode may also be made of an inert substrate plated with the electrode metal, or it may be made in the form of a sheet of the electrode composition, wrapped with gauze of the same composition to increase the electrode area.

The auxiliary electrode does not participate in the reductive process, and so it may be made of any suitable substance which is not attacked by the oxidative side of the electrolytic process. Auxiliary electrodes are most often made of the noble metals, especially platinum, or of carbon. Platinum oxide, or platinum coated with platinum oxide, is the preferred anode composition. Lead oxide, silver oxide and such metallic oxides are also usable auxiliary electrode compositions.

It is most effective to arrange the cell so that the distance between the auxiliary electrode and the working electrode is everywhere the same, and is as small as possible. The relationship is desirable in all electrolytic processes, to maximize current flow and minimize temperature rise caused by the resistance of the fluid to the flow of current.

The process is carried out in an acidic working fluid, which is made acid by the addition of an acid, preferably sulfuric acid or hydrochloric acid, or of a buffering mixture of salts, acids and bases.

The acid condition is necessary to give up protons to the reaction at the working electrode, and also to keep the working fluid acid, because the products are unstable in basic conditions.

If an undivided cell is used, the fluid in contact with both the working electrode and the auxiliary electrode will be the same. If the cell is divided, however, the working fluid will undoubtedly be different from the fluid in the auxiliary electrode compartment.

The working fluid used in this invention may be aqueous, organic or mixed. The organic portions of the working fluid may be either water-miscible or water-immiscible. It is preferred to use a water-miscible solvent, if a mixed system is desired, so that the working fluid is a homogeneous solution.

Suitable water-miscible organic solvents include the amides, especially dimethylformamide and dimethylacetamide, acetone, the water-miscible alkanols, such as methanol, ethanol and propanol, and tetrahydrofuran.

If a water-immiscible solvent is used in the working fluid, the choice of solvents is extremely broad, because any solvent may be used which is not reduced at the working electrode. Especially desirable solvents include the halogenated solvents, such as dichloromethane, 1,1,2-trichloroethane, chloroform, chlorobenzene, 1,1,1-trichloroethane and the like. Other immiscible solvents which may advantageously be used include the ketones including methyl ethyl ketone, methyl butyl ketone and methyl isobutyl ketone, to mention only those which are economically available in commerce, the aromatic solvents such as benzene, toluene and the xylenes, the alkanes such as pentane, hexane and the octanes, the alcohols such as phenol, the butyl alcohols and the like, and ethers such as diethyl ether, diisopropyl ether and hexahydropyran.

An electrolyte may be used as well as the acid or salts which maintain the acidity of the working fluid. Such electrolytes are commonly used in the electrochemical art, and are preferably chosen from the class of quaternary ammonium salts. Useful electrolytes for this purpose include, for example, tetraethylammonium perchlorate, tetrabutylammonium perchlorate, benzotributylammonium chloride, benzyltriethylammonium bromide, benzyltriethylammonium chloride, methyltributylammonium iodide, tribenzylethylammonium p-toluenesulfonate, and the like electrolytes.

If the process is to be carried out in a divided cell, the divider may be made of any of the materials commonly used in electrochemistry for the purpose. Especially useful dividers are made from the ion exchange membranes, especially those which can pass cations. Dividers may also advantageously be made of finely porous substances such as ceramic membranes and sintered glass membranes. Such porous dividers may be made permeable to ions, but not to the fluids themselves, by sealing the membranes with a conductive gel, of which a typical example is agar gel saturated with an ionic substance such as, for example, potassium sulfate.

When the auxiliary electrode occupies a cell compartment by itself, it is immersed in a conductive fluid. If the divider is a porous membrane, it is advisable to provide an auxiliary electrode fluid which is compatible with the working fluid, such as an aqueous solution of the mineral acid used in the working fluid. If the cell divider is porous only to ions, then the auxiliary electrode fluid may be any convenient conductive fluid, such as dilute aqueous solutions of ionizable salts and acids.

The temperature of the process is from about 0° to about 75°, preferably from about 0° to about 30°.

The potential of the working electrode, or the potential between the working electrode and the auxiliary electrode, may be controlled in various ways. The most effective and precise way to control the potential is to use a reference electrode, with its junction to the working fluid placed as physically close as possible to the working electrode. The desired potential for the process is determined from examination of a voltammogram of the system, and the potential between the working electrode and the auxiliary electrode is adjusted to give the desired constant potential between the reference electrode and the working electrode. This method of control is much more effective than control by the overall voltage between the working electrode and the auxiliary electrode, because that voltage depends on the condition of the dividing membrane, if any, the concentration of the acid in the working fluid, and the concentration of the compound to be reduced in the working fluid.

Similarly it is relatively inefficient to control the system by means of the current flow between the auxiliary electrode and the working electrode, because the current flow is directly dependent on the concentration of the compound to be reduced, as well as upon the physical condition of the electrodes and of the divider. However, when an individual reduction has been thoroughly studied and the relationship between current, time and concentration is known, controlled-current electrolysis can be used for production of repeated batches.

Thus, the best way to control the system is by the potential between a reference electrode and the working electrode, and the control most advantageously is provided by an automatic instrument which constantly senses that potential and adjusts the voltage between the working electrode and auxiliary electrode accordingly. Such instruments are now readily available; one maker of them is Princeton Applied Research, Inc., Princeton, N.J., U.S.A.

As has been briefly discussed above, the potential for operating the process with any given combination of electrodes, working fluid and compound is determined according to the routine method of the electrochemical art, by running a voltammogram of the system.

It is not possible, of course, to name a precise potential range for the operation of the process, since the potential for every system will necessarily be different. However, the potential of the working electrode for reductions according to this process is from about −1 volt to about −2 volts, relative to a saturated calomel reference electrode, in the majority of systems.

The reduction appears to be a 2-electron process, and so the reduction of a gram-mole of compound requires 192,974 coulombs. More current is necessary, of course, when the starting compound is a 1-oxide. The length of time necessary to pass this amount of current necessarily depends upon the overall resistance of the cell and the effective area of the electrodes.

Electrolytic cells usually require good agitation, and this process is typical in this respect. It has been found advisable to provide enough agitation of the working fluid to keep the surface of the electrode thoroughly swept, so that a fresh supply of compound to be reduced is constantly supplied to the working electrode. Further, when a water-immiscible solvent is used in the working fluid, it is necessary to agitate the fluid sufficiently well to keep the two phases of the working fluid intimately mixed in the form of fine droplets.

The electrochemical art has long known that electrolytic processes are carried out more advantageously in flow cells than in batch electrolytic cells, in general. A flow cell is an electrolytic cell arranged for the constant passage of the working fluid through the cell. The cell volume may be quite small, and the current density rather high, to achieve the desired extent of reaction in a single pass through the cell, or the flow rate may be lower and the volume larger, with the expectation that a number of passes through the cell will be necessary. In either event, the flow cell is operated continuously with no interruptions for filling and emptying the cell, and the associated operations of product isolation and temperature control are carried on outside the cell.

Flow cells are set up just as are batch cells, except for the necessary provisions for entry and exit of the working fluid. A flow cell may be divided, if necessary, in the usual manner. It is often possible to design a flow cell with the electrodes spaced advantageously close to each other, because the agitation of the working fluid is provided by its own flow velocity and it is unnecessary to provide for mechanical agitation of the cell. For example, a flow cell is often built in the form of a plate-and-frame filter press, with the electrodes in sheet form, clamped between the frames.

The concentration of the compound to be reduced in the working fluid is widely variable and is limited only by the solubility of the compound. Of course, it is most economical to use relatively high concentrations, in order to obtain the maximum effect from the solvents used in the process. However, workup of the fluid and isolation of the product from it is frequently more difficult when highly concentrated working fluids are used. Accordingly, it has not been advantageous in practice to use concentrations of compound in the working fluid higher than about 20% weight/volume.

The 3-acetoxymethyl 7-epi configuration cephem starting compounds are obtained by methods long known to cephalosporin chemists. Kim and McGregor, *J. Antibiotics* 27, 831-33 (1974) show the epimerization of a natural configuration 3-acetoxymethylcephem ester, and show that the 7-amino group remained in the α configuration while the side chain was deacylated and reacylated, and while the ester group was removed. Thus, their epimerization process, consisting of reaction at ambient temperature with diisopropylamine in tetrahydrofuran of the Schiff's base of the formula

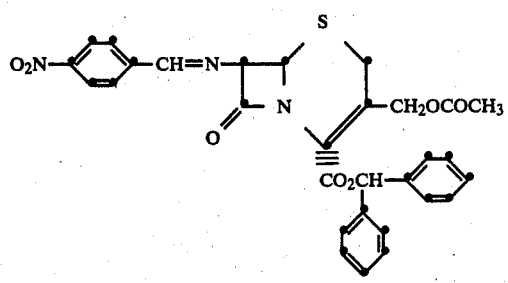

is useful to prepare any desired 7-epi configuration 3-acetoxymethyl starting material, by use of an ultimate starting compound having the desired R and R¹ groups, or by deacylating, acylating, deesterifying or esterifying according to the methods commonly used in cephalosporin chemistry.

Another source of 7-epi configuration 3-acetoxymethyl starting compounds is shown by Sassiver and Shepherd, *Tet. Let.*, 3993-96 (1969), who epimerized the 9-fluorenyl ester of 3-acetoxymethyl-7-β-(thien-2-yl)-3-cephem-4-carboxylic acid, 1-oxide, to the 7-epi configuration by simple contact with triethylamine in dimethyl sulfoxide at 50°. The process of Sassiver and Shepherd, thus, will provide any of the 3-acetoxymethyl starting compounds in the 7-epi configuration, combining their process with the deacylation, acylation, deesterification and esterification processes as commonly used. The sulfoxides provided by Sassiver and Shepherd are most easily reduced to the sulfide form, if desired, by use of Hatfield's acyl bromide/bromine scavenger process, as taught in U.S. Pat. No. 4,044,002. The reduction is preferably carried out with acetyl bromide and a $C_2$-$C_5$ alkene, such as ethylene, in an inert ogranic solvent at −25° to 50°.

Another method of obtaining the compounds of this invention is provided by the process of Chou, described in an application filed on the same day as this application, which application is entitled "Synthesis of a β-lactam sulfinyl chloride".

Chou's process starts with 4-nitrobenzyl 6β-phenoxyacetamidopenam-3-carboxylate, 1-oxide, which is epimerized to the 6α-configuration as by treatment with a silylating agent and a strong base. Most preferably, the natural configuration sulfoxide is treated with a large excess of triethylamine and a large excess of trimethylchlorosilane at moderately low temperatures in the range of about 0° to ambient temperature. It is preferable to use about 5 moles of triethylamine per mole of penicillin sulfoxide, and to carry out the process in an inert organic solvent such as dichloromethane. The epimerization is illustrated by a Preparation below.

The 6-epi penicillin oxide is ring-opened according to Chou's invention to form the sulfinyl chloride of the formula

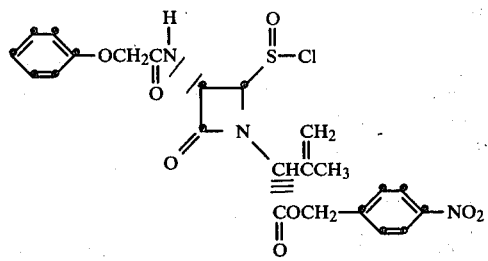

which is then ring-closed to form a 7-epi exomethylenecepham oxide and reduced to a compound of this invention.

Chou's process is carried out in benzene, toluene or a mixture of benzene and toluene. It is most preferred to use as the reaction medium a mixture of equal volumes of benzene and toluene, which mixture provides an ambient pressure reflux temperature of about 92°. The temperature range for the process is from about 80° to about 110°, more preferably from about 85° to about 94°.

The chlorinating agent used to prepare the sulfinyl chloride is N-chlorophthalimide, of which is moderate excess should be used. From about 1.1 to about 1.5 moles of the chlorinating agent per mole of penicillin sulfoxide are used, most preferably from about 1.1 moles to about 1.3 moles. The reaction time is from about 1 to about 3 hours.

It is very important to control the amount of free hydrochloric acid in the reaction mixture, and, accordingly, a very effective acid scavenger is needed. The acid scavenger is a polymer consisting of poly(4-vinylpyridine) cross-linked with from about 2% to about 5% of divinylbenzene. The use of such polymers as acid scavengers is taught in full detail by U.S. Pat. No. 4,289,695, of Chou. The polymer is used in particulate form, having a size distribution from about 20 to about 120 microns, although some part of the particles may be smaller and larger, and a relatively large amount of the polymer should be used, in the range of from about 0.8 gram to about 2 grams per gram of starting penicillin sulfoxide.

It is most important to carry out Chou's process under substantially anhydrous conditions, and to exclude all basic contaminants from the reaction mixture. The maintenance of these necessary conditions is a problem, because the epimerization process which forms the starting compound is carried out in a strong base, and because the purified 6-epi penicillin sulfoxide starting material retains a molecule of water in hydrate from. Thus, it is critical thoroughly to purify and wash the 6-epi penicillin sulfoxide to remove substantially all of the triethylamine or other strong base used in the epimerization.

The molecule of water of hydration attached to the penicillin sulfoxide cannot be removed by ordinary drying processes, and it must therefore be removed from the reaction mixture before the process starts, or else very quickly thereafter. It is preferred to heat the solvent and the polymer to the reflux temperature, and then to add the penicillin sulfoxide while heating is continued. The sulfoxide then dissolves, and the water of hydration leaves the reaction mixture in the form of an azetrope, and can be removed from the reflux returning to the reaction vessel by a conventional water trap, or by other means such as passing the reflux through a water-absorbing medium such as calcium oxide and the like. When the water has been substantially all removed, the N-chlorophthalimide is added and the reaction starts.

Alternatively, if it is desired to add the N-chlorophthalimide and the penicillin sulfoxide at the same time, or to add the penicillin sulfoxide as the last addition to the reaction mixture, it is quite necessary to have the mixture vigorously refluxing before the penicillin sulfoxide is added, so that its water of hydration will be thoroughly and quickly removed as fast as it dissolved.

Further alternatively, if it should be necessary in a particular instance to avoid refluxing the reaction mixture, it can be dried in the reaction vessel by other known means, such as by the addition of molecular sieves, water-absorbing inorganic salts, phosphorus oxides or other known dehydrating agents to the reaction mixture. Such expedients, however, are by no means preferred and the use of azeotropic distillation, as described above, is the preferred method for obtaining the necessary substantially anhydrous conditions.

The sulfinyl chloride so obtained is ring-closed according to the process of U.S. Pat. Nos. 4,052,387 and 4,190,724. Thus, the epi sulfinyl chloride is reacted with a Lewis acid or proton acid Friedel-Crafts catalyst, or a metathetic cation-forming agent to form a complex. The preferred reagent is stannic chloride; other typical reagents include, e.g., zinc chloride, zinc bromide, titanium tetrachloride, methanesulfonic acid, trifluoroacetic acid, phosphoric acid, sulfuric acid, polyphosphoric acid, silver toluenesulfonate, silver perchlorate and the like. It is preferred to form the complex in a dry organic solvent, most preferably toluene or benzene, in the presence of an oxo ligand. Diethyl ether is the preferred ligand, and acetone, diethyl ketone, tetrahydrofuran, dioxane, cyclohexanone, triphenylphosphine oxide and the like are further typical ligands. The resulting insoluble complex cyclizes to the exomethylenecepham in the solid state, and is then decomposed with a hydroxy-containing compound, preferably methanol, to provide the desired product. The examples below further illustrate the process.

The 7-epi exomethylenecepham sulfoxide so obtained is reduced to a compound of this invention by reducing it, as by the acyl bromide/bromine scavenger technique of Hatfield, U.S. Pat. No. 4,044,002, described above.

Still further, the compounds of this invention, other than the specific compound prepared by Chou's invention described above, can be prepared by the general process of U.S. Pat. Nos. 4,052,387, 4,081,440 and 4,190,724. Accordingly, a 6-epi penicillin sulfoxide having the desired R and $R^1$ groups is reacted with an N-chlorohalogenating agent at 75° to 135° under anhydrous conditions. Halogenating agents include ureas, amides, imides, urethanes, sulfonamides, and the like, most preferably the imides such as N-chlorosuccinimide, N-chloroglutarimide and especially N-chlorophthalimide. The reaction is done in an inert organic solvent, preferably an aromatic solvent, and a non-alkaline acid scavenger is preferably in the reaction mixture; epoxides and alkaline metal oxides, and especially the vinylpyridine polymer discussed above, are suitable scavengers.

The epi sulfinyl chloride so produced is cyclized as discussed above under the discussion of Chou's process to form the 7-epi exomethylenecepham sulfoxide, and reduced as discussed above to form the desired product of this invention.

Compounds wherein $R^1$ is hydrogen may be recovered and isolated as the acid, or as a salt, in the usual way. That is, when a salt is desired, the compound is isolated from a solution of the appropriate base in water or a suitable solvent such as a low molecular weight ketone or alcohol, or an aqueous ketone or alcohol.

Compounds wherein R is hydrogen are best obtained by deacylating a corresponding compound wherein R is an acid residue. The deacylation may be performed by conventional methods, such as the processes taught by U.S. Pat. Nos. 3,697,515, 3,875,151, 3,957,771, 4,021,426, 3,234,223 and the like. In general, such compounds are deacylated by reacting the 7-α-amido compound with a halogenating agent which can form an imido halide, such as an acid halide, especially phosphorus pentachloride, in the presence of a tertiary amine. The imido halide is converted to an imido ether by reaction with an alcohol, especially a lower alkanol such as methanol, and hydrolyzed to form the 7-α-amino compound with water, an alcohol or an aqueous alcohol.

The compounds of this invention are best used in a process which is more fully described in an application of Kukolja and Pfeil, entitled Preparation of Oxazolinoazetidinones, which application was filed on the same day as the present application. That process reacts this invention's 7-epi configuration exomethylenecephams first with molecular chlorine and then with a tri(alkyl or phenyl)phosphine to prepare an oxazolinoazetidinone of the formula

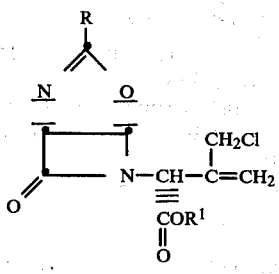

The above group of compounds are known intermediates used in the synthesis of oxa-β-lactam antibiotics, as shown by publications such as U.S. Pat. No. 4,220,766 and South African Pat. No. 77/7646, both of Shionogi and Company. The Preparations below further illustrate the synthesis of the oxazolinoazetidinones from the compounds of this invention.

The process is carried out in an inert organic solvent, preferably in a halogenated organic solvent such as dichloromethane, 1,1,2-trichloroethane, chloroform, 1,2-dichloroethane, chlorobenzene, the various dichlorobenzenes, 1,2-dibromoethane, and the like. Solvents can also be chosen from the aromatics such as benzene, toluene and the xylenes.

The chlorination step of the process is carried out at a very low temperature such as from about $-100°$ to about $-20°$, preferably from about $-100°$ to about $-60°$. The reaction with the phosphine is carried out at more moderate temperatures from about $-50°$ to about $50°$, preferably from about $0°$ to the ambient temperature. By ambient temperature is meant temperatures such as are normally encountered in occupied buildings, such as from about $15°$ to about $35°$.

It is important to carry out the process under substantially anhydrous conditions. It has been found advisable to dry the solvent very carefully, as by contact with molecular sieves, or by azeotropic distillation, if the solvent lends itself to it. Because of the very low temperatures of the process, condensation in the vessel is a possible problem, and must therefore be avoided by use of drying tubes or columns.

In the preferred practice, the 7-epi exomethylenecephem is dissolved in an appropriate amount of solvent. The concentration of the reactant is not critical, but may be chosen for convenience in a given set of circumstances. Molecular chlorine is then added, either by bubbling through the solution, or as a solution in additional solvent. No unusual excess of chlorine is needed. Approximately 1 mole of $Cl_2$ per mole of starting compound is adequate; small excesses in the range of from a few percent to 20 percent will increase the yield, and very large excesses, even up to 10X, are not harmful. The mixture is then stirred at constant temperature for a relatively brief period of time until the reaction has gone to the desired degree of completion. An operator may wish to maximize the yield of the process by using relatively long reaction times, or to maximize throughout of product, by minimizing reaction times.

The phosphine is then added to the first reaction mixture. A molar amount of the phosphine, or a small to moderate excess as discussed above, may be used. It is preferred to warm the mixture after the addition of the phosphine to a higher temperature as described above, or alternatively to turn off the cooling and allow the mixture to warm naturally toward the ambient temperature.

The following Preparations and Examples are provided to assure that the reader of this document fully understands the invention, and how to obtain and use the compounds of the invention.

The first two Preparations immediately below illustrate the process of Chou for preparing an epi configuration sulfinyl chloride, as discussed above.

Preparation 1

4-Nitrobenzyl 6-α-phenoxyacetamidopenam-3-carboxylate, 1-oxide

A 250 g. portion of 4-nitrobenzyl 6-β-phenoxyacetamidopenam-3-carboxylate, 1-oxide, was dissolved in 1750 ml. of dichloromethane, and was cooled to $0°$–$5°$. The temperature was held constant while 272.5 ml. of triethylamine was added over 15 minutes. The mixture was stirred for 15 minutes, and then 214 ml. of trimethylchlorosilane and 70 ml. of additional triethylamine were added, and the mixture was stirred for 5 hours, still at constant temperature. To the mixture was then added slowly 175 ml. of acetic acid, and the temperature was allowed to rise to $20°$–$25°$. It was then washed twice with 1000 ml. portions of water, and then with 1000 ml. of 5% aqueous sodium carbonate. Five hundred ml. of additional dichloromethane was added, and the water layers were combined and extracted twice with 250 ml. portions of dichloromethane. All of the organic layers were combined, and chilled overnight. The crude product was isolated by filtration, and dried to obtain 92.9 g. of the desired product. An additional 80.8 g. of crude product was obtained by evaporating the solvent from the filtrate, dissolving the resulting gum in 100 ml. of acetone, and crystallizing the product from it by chilling, seeding and the addition of a small amount of water. The portions of product were recrystallized by dissolving each in 600 ml. of warm acetone, filtering the warm solution, chilling the filtrate, and washing the resulting crystals with dichloromethane. A total yield of 156.7 g. of recrystallized product was obtained, having a melting range of 123°–125° and 122°–124° in the two sections.

Preparation 2

4-Nitrobenzyl 2-(2-oxo-3-α-phenoxyacetamido-4-chlorosulfinylazetidino)-3-methyl-3-butenoate To a 1000 ml. flask were added 500 ml. of benzene and 12.5 g. of poly(4-vinylpyridine)polymer, cross-linked with 5% of divinylbenzene, in the form of a powder substantially all of which passed a 120-mesh screen. The suspension was heated to the reflux temperature, and the reflux was returned to the flask through a water trap until no more water was collected. The suspension was then cooled slightly, and to it were quickly added 12.5 g. of the product of Preparation 1 and 5.5 g. of N-chlorophthalimide. The mixture was quickly heated back to the reflux temperature and heated at that temperature for 5 hours, while the reflux was returned through a water trap to the flask.

The mixture was then cooled to 0°–5° and filtered, to obtain a benzene solution of the desired sulfinyl chloride, containing considerable starting compound. The presence of the desired product was confirmed by nuclear magnetic resonance analysis on a 60 mHz instrument. The following features are characteristic: δ1.80 (s, 3H, —CH$_3$); 4.50 (s, 2H, —OCH$_2$—); 5.05(s) and 5.05–5.30 (m, 3H total, H2 and =CH$_2$ of butenoate); 5.30 (s, 2H, —CO$_2$CH$_2$—); 5.77 (d, 1H, J=2 cps, H4 of azetidine); 5.93 (dd, 1H, J=2 cps, H3 of azetidine); 7.73 (bs, 1H, —NH—); 6.73–7.37 (m, 5H, phenoxy aromatic); 7.5–8.17 (2d, 4H, J=9 cps, benzyl aromatic)

EXAMPLE 1

4-Nitrobenzyl 7-α-phenoxyacetamido-3-exomethylenecepham-4-carboxylate, 1-oxide

To the product solution above was added 1.6 ml. of diethyl ether and 5.85 ml. of stannic chloride, and the mixture was stirred for 16 hours at ambient temperature. The resulting complex was isolated by filtration and washed with hexane, and the washed filter cake was added to 75 ml. of methanol and agitated. After 30–45 minutes of stirring, the solution was placed in an ice bath and stirred there for 6 hours. The crystalline product was filtered and washed with methanol to obtain 4.6 g. of the desired 7-epiexomethylenecepham sulfoxide, m.p. 190.5°–191.5°.

Preparation 3

4-Nitrobenzyl 2-(2-oxo-3-α-phenoxyacetamido-4-chlorosulfinylazetidino)-3-methyl-3-butenoate The process of Preparation 2 was followed, in general, except that the solvent was a mixture of 250 ml. of benzene, carefully azeotropically distilled to eliminate water, and 250 ml. of toluene. The reaction temperature was the reflux temperature of the mixture, 92°, and reflux was continued for 2 hours and 20 minutes. The resulting solution of the sulfinyl chloride, when analyzed by nuclear magnetic resonance analysis, was found to contain very little starting compound.

EXAMPLE 2

4-Nitrobenzyl 7-α-phenoxyacetamido-3-exomethylenecepham-4-carboxylate, 1-oxide

The product solution from Preparation 3 was subjected to the process of Example 1, except that 100 ml. of methanol was used, to obtain 7.1 g. of the desired 7-epi exomethylenecephem sulfoxide, m.p. 185°–189.5° C.

Preparation 4

4-Nitrobenzyl 2-(2-oxo-3-α-phenoxyacetamido-4-chlorosulfinylazetidino)-3-methyl-3-butenoate The process of Preparation 3 was followed, on a scale twice as large, except that reflux was continued for 2 hours 45 minutes. Nuclear magnetic resonance analysis of the product solution showed that essentially all of the starting compound had been consumed.

EXAMPLE 3

4-Nitrobenzyl 7-α-phenoxyacetamido-3-exomethylenecepham-4-carboxylate, 1-oxide

The process of Example 1 was followed using the product solution of Preparation 4 on a scale twice as large as Example 1, to obtain 14.6 g. of the expected product, m.p. 182°–188° after drying.

Preparation 5

4-Nitrobenzyl 2-(2-oxo-3-α-phenoxyacetamido-4-chlorosulfinylazetidino)-3-methyl-3-butenoate The process of Preparation 4 was followed again, except that the reflux time was only 2 hours 30 minutes. The resulting product solution was found by nuclear magnetic resonance analysis to contain very little starting compound.

EXAMPLE 4

4-Nitrobenzyl 7-α-phenoxyacetamido-3-exomethylenecepham-4-carboxylate, 1-oxide

The process of Example 3 was followed again on the product solution of Preparation 5, except that 4.15 ml. of diethyl ether was used instead of 3.6 ml. A 14.9 g. portion of the desired product, m.p. 189°–191° after drying, was obtained.

Preparation 6

4-Nitrobenzyl 7-α-phenoxyacetamido-3-exomethylenecepham-4-carboxylate

A 1.0 g. portion of 4-nitrobenzyl 7-α-phenoxyacetamido-3-exomethylenecephem-4-carboxylate, 1-oxide, was dissolved in 30 ml. of dichloromethane, and the solution was cooled to 0°–5°. To it was added 1.06 ml. of 2-methyl-2-butene and 0.33 ml. of acetyl bromide, and the mixture was stirred at 0°–5° for 90 minutes. The mixture was then quenched by the addition of a large amount of water, and the organic layer was separated. It was then washed twice with 20 ml. portions of water and once with saturated sodium chloride solution, and was dried over magnesium sulfate. The product was isolated by low pressure high performance liquid chromatography on a silica gel column, using a 1:1 mixture of acetonitrile and water as the eluant. The product-containing fraction was evaporated to dryness under vacuum to obtain a small amount of the expected product.

The next two Examples illustrate the preparation of typical compounds of this invention by electrolytic reduction of 3-acetoxymethyl starting compounds.

EXAMPLE 5

7-α-(4-methylphenylformamido)-3-exomethylenecepham-4-carboxylic acid

An electrolytic cell having a total volume of 50 ml. was set up with a toroidal mercury working electrode having an area of 14 cm.$^2$. The auxiliary electrode was a loop of platinum wire placed parallel to the surface of the working electrode and separated from it by a fine glass frit. The reference electrode was a saturated calomel electrode, with its junction placed very close to the surface of the working electrode.

The cell was charged with 50 ml. of 1-molar pH 4.0 McIlvaine buffer containing 876 mg. of 7-α-(4-methylphenylformamido)-3-acetoxymethyl-3cephem-4-carboxylic acid.

An automatic potentiostat was used to control the potential between the working electrode and the reference electrode at −1.6 volt. The electrolysis was continued for 233 minutes while the temperature was controlled at 25°. The working fluid was then washed out of the cell with deionized water, made acid to about pH 2, and extracted with ethyl acetate. The organic layer was dried and evaporated to dryness under vacuum to obtain 356 mg. of the desired product in impure form as identified by n.m.r. spectroscopy in d$_6$ acetone. δ2.37 (2, 3H, —CH$_3$); 3.37, 3.71 (AB, J=14 Hz, 2H, H2 of thiazine); 5.23 (m, 5H, =CH$_2$, H4, H6, H7); 7.26, 7.84 (AB, J=8 Hz, 4H, aromatic)

EXAMPLE 6

7-α-(4-methylphenylformamido)-3-exomethylenecepham-4-carboxylic acid

The process of Example 5 was used again in large part, with a sample of 406 mg. of the starting compound, in the 1-oxide form, in a total volume of 35 ml. of working fluid. The electrolysis was continued for 167 minutes, at the end of which time the pH of the working fluid was 5.5. The working fluid was then rinsed out of the cell with deionized water, layered with 60 ml. of ethyl acetate, and adjusted to pH 1.7 with concentrated sulfuric acid. The aqueous layer was extracted again with an additional 60 ml. of ethyl acetate, and the combined organic layers were dried over sodium sulfate and evaporated to a solid under vacuum to obtain 330 mg. of impure product.

The following preparation illustrates the use of the compounds of this invention as starting compounds for the synthesis of useful oxazolinoazetidinones.

Preparation 7

Diphenylmethyl 3-chloromethyl-2-[3-(4-methylphenyl)-7-oxo-epi-4-oxa-2,6-diazabicyclo[3,2,0]-hept-2-ene-6-yl]-3-butenoate A 150 mg. portion of diphenylmethyl 7-α-(4-methylphenylformamido)-3-exomethylenecephem-4-carboxylate was dissolved in 20 ml. of dichloromethane, which had been stabilized with cyclohexane and dried over molecular sieves. The solution was chilled in a dry ice-acetone bath to about −78°, and 0.33 ml. of 1-molar chlorine gas in dichloromethane was added. The mixture was stirred at constant temperature for 45 minutes, and 86 mg. of triphenyl phosphine was added. The cooling bath was then removed, and the solution was stirred for two hours. The volatiles were evaporated away under vacuum, and the gummy residue was purified by chromatography over 3.5 g. of silica gel under about 5 psi of nitrogen pressure, eluting with a gradient solvent ranging from pure toluene to 5% ethyl acetate in toluene. The product-containing fractions were combined and evaporated to obtain 60 mg. of the desired product, which was identified by nuclear magnetic resonance analysis in CDCl$_3$, using trimethylsilane as the internal standard. δ2.37 (s, 3H, CH$_3$); 4.07 (s, 2H, CH$_2$Cl); 5.03, 5.20, 5.45 (s, 3H, =CH$_2$ and H4); 5.22, 5.87 (d, J=4 Hz, 2H, β-lactam); 6.80 (s, 1H, CHPh$_2$); 7.08, 7.66 (AB, J=8 Hz, aromatic of amide); 7.20 (s, 10H, aromatic of ester).

We claim:

1. A 7-epi-exomethylenecepham of the formula

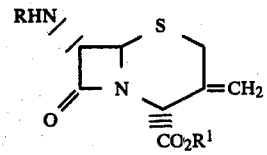

wherein R is hydrogen or an acyl group conventionally used in the cephalosporin art and derived from a carboxylic acid, and R$^1$ is hydrogen, a carboxy-protecting group, or a salt-forming cation.

2. A compound of claim 1 wherein R is hydrogen or the formula R$^2$OC, wherein R$^2$ is hydrogen, C$_1$–C$_3$ alkyl, cyanomethyl, benzyloxy, 4-nitrobenzyloxy, t-butoxy, 2,2,2-trichloroethoxy, 4-methoxybenzyloxy, or the group R$^3$, in which R$^3$ is phenyl or phenyl substituted by 1 or 2 halogen, protected hydroxy, nitro, cyano, trifluoromethyl, C$_1$–C$_4$ alkyl or C$_1$–C$_4$ alkoxy groups; or R$^2$ is a group of the formula R$^4$—(O)$_n$—CH$_2$—, in which R$^4$ has the same meanings as R$^3$ above, or is 1,4-cyclohexadienyl, 2-thienyl or 3-thienyl; n is 0 or 1; provided that when n is 1, R$^4$ has the same meanings as R$^3$; or R$^2$ is a group of the formula R$^4$—CH(W)—, wherein R$^4$ has the same meanings as defined above, and W is protected hydroxy or protected amino.

3. A compound of claim 2 wherein R$^2$ is C$_1$–C$_3$ alkyl, phenyl, phenoxy, benzyl or phenyl substituted with C$_1$–C$_4$ alkyl.

4. A compound of any one of claims 1, 2 or 3 wherein R$^1$ is acetoxymethyl, 1-acetoxyethyl, pivaloyloxymethyl, 1-pivaloyloxyethyl, carboethoxyoxymethyl, 1-carboxyethoxyoxyethyl, phthalidyl, diphenylmethyl, nitrobenzyl, tert-butyl, methoxybenzyl, trichloroethyl, or methyl.

5. A compound of any one of claims 1, 2 or 3 wherein $R^1$ is hydrogen.

6. A compound of claim 1 wherein R is hydrogen.

7. A compound of claim 1 wherein R is phenoxyacetyl.

8. A compound of claim 1 wherein R is phenylacetyl.

9. A compound of claim 1 wherein R is 4-methylphenylformyl.

10. A compound of any one of claims 6, 7, 8, or 9 wherein $R^1$ is hydrogen.

11. A compound of any one of claims 6, 7, 8 or 9 wherein $R^1$ is 4-nitrobenzyl.

12. A compound of any one of claims 6, 7, 8 or 9 wherein $R^1$ is 4-methoxybenzyl.

13. A compound of any one of claims 6, 7, 8 or 9 wherein $R^1$ is diphenylmethyl.

14. A compound of any one of claims 6, 7, 8 or 9 wherein $R^1$ is 2,2,2-trichloroethyl.

* * * * *